United States Patent [19]

Parmelee et al.

[11] Patent Number: 5,589,397
[45] Date of Patent: Dec. 31, 1996

[54] METHOD FOR MONITORING THE PERFORMANCE OF AN AMINO ACID SEQUENCER

[75] Inventors: David C. Parmelee, Rockville, Md.; Salvatore Sechi, Washington, D.C.

[73] Assignee: The United States of America as represented by the Department of Health and Human Services, Washington, D.C.

[21] Appl. No.: 384,212

[22] Filed: Feb. 6, 1995

Related U.S. Application Data

[62] Division of Ser. No. 920,130, Jul. 24, 1992, abandoned.

[51] Int. Cl.$^6$ ................................................. G01N 33/48
[52] U.S. Cl. ................................................. 436/89; 436/86
[58] Field of Search ............... 514/11–13; 530/324–326; 436/89, 86

[56] References Cited

U.S. PATENT DOCUMENTS 4,693,993  9/1987  Stewart ........................................ 514/14

OTHER PUBLICATIONS

Spatola *Chem & Biochem* of Amino Acids, Peptides and Proteins pp. 267–357, 1983.
"STN Publication" From a Manual Published by STN International, Chem Abstracts Service, Columbus, Ohio.

BIOSIS 94:266097.

BIOSIS 93:339070.

Product Bulletin, "FMOC Multiple Antigenic Peptide (MAP) Resins", *Applied Biosystems* (1992).

James Bausch et al., "Automated Protein Microsequencing: Using an Amino Acid Homopolymer as an Internal Standard", *Biopharm* (1989).

Michael W. Hunkapiller, "PTH Amino Acid Analysis", *Applied Biosystems, Inc.*, 14:1–27 (Nov. 18, 1985).

*Primary Examiner*—Lyle A. Alexander
*Attorney, Agent, or Firm*—Needle & Rosenberg, P.C.

[57] ABSTRACT

The present invention further provides novel synthetic control peptides containing from about 3 to 100 natural amino acid residues that are designed for use in monitoring the proper operation of amino acid sequencers and to monitor peptide or protein cleavage reactions. The control peptide, or mixture of control peptides, are designed to obtain data for many or all common, uncommon and difficult to measure amino acids within 15 sequencer cycles and to provide cleavage sites for at least 4 different amino acid cleavage reactants.

11 Claims, 12 Drawing Sheets

SEQ. ID NO. 3

D C L K V W G D S T K V L E N R F Y L K A I R V H L K

SEQ. ID NO. 4

K A E F H L R F E M A R F D P L K I Q F V D K A Y F K

● Difficult Amino Acids

Repetitive Yields

FIG. 7

SEQ. ID NO.3

D C L K V W G D S T K V L E N R F Y L K A I R V H L K

Alkylation  — C ─────────────────────────────────────
              |
              CM (or PE)

Skatole     ──────── W* 
                                                              ──────────────── K Asn-C       ──────────────────── N
                                              ──────────────── K Trypsin     ──── K ──────── K ──── R ──── K ─ R ──── K Lys-C       ──── K ──────── K ──── R ──── K
                                              ─ R ──── K Arg-C       ──── K ──────── K ──── R ──────────── K
                                    ──── K ─ R

V8-E-AB     D ──────── D ──────── E ──────────── K

V8-DE-PO$_4$  D ─ ──────── E ──────────── K
                   ──── D

Asp-N       D ────────
                   ──── D ──────────────────── K

FIG. 9

SEQ. ID NO.4

K A E F H L R F E M A R F D P L K I Q F V D K A Y F K

| | | |
|---|---|---|
| CNBr | ——————— M* | |
| | | ——————————————— K |
| HCOOH | ——————— D | |
| | P ——————— K | |
| Trypsin | K- ——— R ——— K | |
| | ——— R ——k ——— K | |
| Lys-C | K- ——— K | |
| | ——— R — R — K ——— K | |
| Arg-C | K ——— R ——— K ——— K — K | |
| | ——— R | |
| V8-E-AB | ——— E ——— D ——— D ——— K | |
| | ——— E | |
| V8-DE-PO₄ | ——— E ——— D ——— K | |
| | ——— E ——— D | |
| Asp-N | ——— E ——— E ——— D ——— K | |
| | D ——— | |

FIG. 10

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1..28
  ( D ) OTHER INFORMATION: /note= "Change all occurrences of
   Lys to Orn"

( i x ) FEATURE:
  ( A ) NAME/KEY: Modified-site
  ( B ) LOCATION: 2..22
  ( D ) OTHER INFORMATION: /note= "Change all occurrences of
   Val to Nvl"

( i x ) FEATURE:
  ( A ) NAME/KEY: Modified-site
  ( B ) LOCATION: 3..23
  ( D ) OTHER INFORMATION: /note= "Change all occurrences of
   Leu to Nle"

( i x ) FEATURE:
  ( A ) NAME/KEY: Modified-site
  ( B ) LOCATION: 4..26
  ( D ) OTHER INFORMATION: /note= "Change all occurrences of
   Ala to Aab"

( x i ) SEQUENCE DESCRIPTION: SEQ ID NO:1:

```
Lys  Val  Leu  Ala  Lys  Val  Ala  Lys  Val  Ala  Lys  Val  Leu  Ala  Lys  Val
1                  5                           10                         15

Ala  Lys  Val  Ala  Lys  Val  Leu  Lys  Lys  Ala  Lys  Lys
               20                      25
```

( 2 ) INFORMATION FOR SEQ ID NO:2:

( i ) SEQUENCE CHARACTERISTICS:
  ( A ) LENGTH: 35 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1..35
  ( D ) OTHER INFORMATION: /note= "Change all occurrences of
   Lys to Orn"

( i x ) FEATURE:
  ( A ) NAME/KEY: Modified-site
  ( B ) LOCATION: 2..30
  ( D ) OTHER INFORMATION: /note= "Change all occurrences of
   Leu to Nle"

( i x ) FEATURE:
  ( A ) NAME/KEY: Modified-site
  ( B ) LOCATION: 3..29
  ( D ) OTHER INFORMATION: /note= "Change all occurrences of
   Val to Nvl"

( i x ) FEATURE:
  ( A ) NAME/KEY: Modified-site
  ( B ) LOCATION: 4..33

(D) OTHER INFORMATION: /note= "Change all occurrences of Ala to Aab"

(xi) SEQUENCE DESCRIPTION: SEQ ID NO:2:

| Lys | Leu | Val | Ala | Lys | Val | Ala | Lys | Val | Leu | Ala | Lys | Val | Ala | Lys | Val |
|---|---|---|---|---|---|---|---|---|---|---|---|---|---|---|---|
| 1 | | | | 5 | | | | | 10 | | | | | 15 | |

| Ala | Lys | Val | Leu | Ala | Lys | Val | Ala | Lys | Val | Ala | Lys | Val | Leu | Lys | Lys |
|---|---|---|---|---|---|---|---|---|---|---|---|---|---|---|---|
| | | | 20 | | | | | 25 | | | | | 30 | | |

| Ala | Lys | Lys |
|---|---|---|
| | | 35 |

(2) INFORMATION FOR SEQ ID NO:3:

(i) SEQUENCE CHARACTERISTICS:
  (A) LENGTH: 27 amino acids
  (B) TYPE: amino acid
  (D) TOPOLOGY: linear (ii) MOLECULE TYPE: peptide (xi) SEQUENCE DESCRIPTION: SEQ ID NO:3:

| Asp | Cys | Leu | Lys | Val | Trp | Gly | Asp | Ser | Thr | Lys | Val | Leu | Glu | Asn | Arg |
|---|---|---|---|---|---|---|---|---|---|---|---|---|---|---|---|
| 1 | | | | 5 | | | | | 10 | | | | | 15 | |

| Phe | Tyr | Leu | Lys | Ala | Ile | Arg | Val | His | Leu | Lys |
|---|---|---|---|---|---|---|---|---|---|---|
| | | | 20 | | | | | 25 | | |

(2) INFORMATION FOR SEQ ID NO:4:

(i) SEQUENCE CHARACTERISTICS:
  (A) LENGTH: 27 amino acids
  (B) TYPE: amino acid
  (D) TOPOLOGY: linear (ii) MOLECULE TYPE: peptide (xi) SEQUENCE DESCRIPTION: SEQ ID NO:4:

| Lys | Ala | Glu | Phe | His | Leu | Arg | Phe | Glu | Met | Ala | Arg | Phe | Asp | Pro | Leu |
|---|---|---|---|---|---|---|---|---|---|---|---|---|---|---|---|
| 1 | | | | 5 | | | | | 10 | | | | | 15 | |

| Lys | Ile | Gln | Phe | Val | Asp | Lys | Ala | Tyr | Phe | Lys |
|---|---|---|---|---|---|---|---|---|---|---|
| | | | 20 | | | | | 25 | | |

(2) INFORMATION FOR SEQ ID NO:5:

(i) SEQUENCE CHARACTERISTICS:
  (A) LENGTH: 25 amino acids
  (B) TYPE: amino acid
  (D) TOPOLOGY: linear (ii) MOLECULE TYPE: peptide (xi) SEQUENCE DESCRIPTION: SEQ ID NO:5:

| Val | Leu | Ile | Val | Trp | Cys | Asp | Ser | Thr | Asn | Leu | Ile | Val | Gly | Glu | Gln |
|---|---|---|---|---|---|---|---|---|---|---|---|---|---|---|---|
| 1 | | | | 5 | | | | | 10 | | | | | 15 | |

| Lys | Tyr | Ala | Leu | Lys | Ile | Val | Gly | Lys |
|---|---|---|---|---|---|---|---|---|
| | | | 20 | | | | | 25 |

(2) INFORMATION FOR SEQ ID NO:6:

(i) SEQUENCE CHARACTERISTICS:
  (A) LENGTH: 25 amino acids
  (B) TYPE: amino acid
  (D) TOPOLOGY: linear (ii) MOLECULE TYPE: peptide (xi) SEQUENCE DESCRIPTION: SEQ ID NO:6:

```
Phe  Ala  Tyr  Phe  His  Leu  Arg  Phe  Val  Met  Ala  Tyr  Phe  Pro  Leu  Phe
1                   5                        10                       15

Lys  Ile  Val  Phe  Lys  Ala  Tyr  Phe  Lys
               20                        25
```

METHOD FOR MONITORING THE PERFORMANCE OF AN AMINO ACID SEQUENCER

This application is a division of application Ser. No. 07/920,130, filed Jul. 24, 1992 now abandoned.

BACKGROUND OF THE INVENTION

The present invention relates to novel peptides useful in the amino acid sequencing context and methods of their use. In particular, this invention relates to an internal standard for amino acid sequencing comprising unnatural amino acid residues that is capable of being sequenced simultaneously with an unknown peptide or protein without interfering with the analysis. Further, this invention relates to synthetic control peptides comprising natural amino acid residues that are designed for use in monitoring the proper operation of amino acid sequencers and for confirming that the system properly identifies all the common amino acid residues. These synthetic control peptides can also be used as controls in a wide variety of chemical and enzymatic reactions to monitor cleavage and modification reactions.

Amino acid sequencers typically degrade a protein or peptide selectively and sequentially into amino acid residues, or derivatives of these residues, that are capable of being qualitatively and quantitatively identified. For instance, the commonly used Edman sequential degradation involves the organic base catalyzed selective coupling of a peptide's N-terminal amino acid with phenylisothiocyanate. The derivatized amino acid is then cleaved from the peptide by treatment with a strong organic acid, typically as an anilinothiazolinone (ATZ) derivative. Repetitive coupling/cleavage cycles at the newly-formed N-terminal amino acid left by the previous cycle provide for sequential separation of the amino acid residues that form the primary structure of the peptide. To determine the identity of the separated derivatives, the ATZ derivative is typically converted to a more stable phenylthiohydantoin (PTH) derivative prior to analysis. These PTH derivatives can then be identified by a variety of analytical procedures, such as by HPLC. The coupling/cleavage cycles, the PTH derivatization procedures and the injection of the PTH derivatives onto an HPLC can be accomplished manually or, more commonly, by fully automated amino acid sequencers as described, for instance, in Applied Biosystems User Bulletin Issue No. 14 (Nov. 18, 1985).

Current internal standards available for use in an amino acid sequencer suffer from various disadvantages. For instance, addition of a synthetic PTH amino acid derivative, such as PTH-norleucine, to one of the sequencer solvents is known. This type of internal standard, however, is capable of indicating only that the sample was injected properly onto the HPLC column. A faulty injection step is only one of a multitude of possible malfunctions that could occur during the sequencing process. For instance, the use of a PTH-amino acid internal standard provides no information regarding whether the equipment is capable of actually sequencing a sample. In addition, the PTH-norleucine derivative is unstable and must be added every 2–3 days, making quantification very difficult and wasting expensive sequencer solvents.

Bausch et al., *BioPharm* 2(5):40–43 (1989) disclose the use of poly-L-ornithine hydrochloride as an internal standard during automated protein microsequencing. The poly-ornithine molecule, which ranges in size from about 15,000 to 30,000 Daltons, degrades to provide a PTH derivative that has a unique chromatographic retention time. Thus, observance of the PTH-ornithine peak (or lack of the peak) for each sequencer cycle during the sequencing of an unknown protein provides information regarding instrument failure, "bad" reagents and sample-specific problems such as N-terminal blockage. However, because poly-ornithine is a homopolymer, this internal standard is incapable of providing information regarding repetitive yield, which is an important index of sequencer performance. Further, because the PTH-ornithine derivative is produced in each sequencer cycle, this internal standard is extremely susceptible to lag, or carryover from preceding cycles due to incomplete degradation, rendering quantifying the PTH-ornithine peaks relatively meaningless. Additionally, while the use of poly-ornithine as an internal standard provides some information regarding instrument failure for a particular cycle or N-terminal protein blockage, this internal standard is incapable of distinguishing between a blank cycle caused by a missed injection and a blank cycle caused by faulty delivery of chemicals during the sequencer reactions. Without this knowledge, the experiment would have to be repeated, which may not be possible for proteins that are only available in minute quantities. Lastly, the poly-ornithine internal standard is more similar in size to a protein rather than a peptide and, thus, is not as easily washed from the sample support as a peptide sample. Consequently, sequencer conditions which provide for optimized sequencing of the poly-ornithine standard may not be appropriate for sequencing an unknown peptide.

Thus, there exists a need for an internal standard for amino acid sequencing that does not interfere with the sequencing of an unknown protein or peptide and can distinguish between a blank sequencer cycle caused by the presence of modified amino acids or machine malfunctions, including blank cycles caused by missed injections and blank cycles caused by faulty delivery of chemicals during the sequencer reactions. There also exists a need for an internal standard in which lag does not interfere with subsequent chromatographic peaks and which provides initial yield and several accurate repetitive yields during the actual analysis of the sample unknown. Additionally, there exists a need for an internal standard having a molecular weight similar to peptides to provide a more accurate correlation when sequencing these components.

Mixtures containing stable PTH amino acid residues, N,N'-diphenylthiourea (DPTU), dithiothreitol (DTT) and/or N,N-dimethyl-N'-phenylthiourea (DMPTU) have been used to optimize the separation conditions needed for resolution of the PTH derivatives by the chosen analytical procedure, such as by HPLC. However, these procedures optimize only the final identification step rather than providing guidance for proper conditions throughout the repetitive coupling/cleavage/derivatization/identification cycles. Proteins, such as β-lactoglobulin, have also been used to verify the operation of the amino acid sequencer. However, optimization of the sequencer using high molecular weight components such as proteins can result in inappropriate operating conditions for sequencing lower molecular weight peptides, including conditions which result in the peptide being "washed out" from the glass filter disc of the amino acid sequencer. Thus, even though β-lactoglobulin contains appropriate amino acid residues suitable for at least three determinations of the repetitive yield, these repetitive yield values may be inapplicable for peptide unknowns. Further, no single peptide is available that has even a few of the uncommon or difficult to measure amino acids sufficiently close to the N-terminus to provide for sequencer optimization that takes into account these residues while still providing information regarding the common amino acids. Thus, there exists a need for a synthetic control peptide, or a mixture of synthetic control peptides, capable of being used to monitor the proper operation of an amino acid sequencer so as to allow optimization of the sequencer with respect to the sequencing of peptides. In particular, there exists a need for control peptides designed to monitor the sequencing of the common amino acids as well as the rarely seen or difficult to measure amino acids in addition to providing an appropriate residue structure and sequence to allow accurate determination of lag and repetitive yield.

While it is possible to use existing proteins and peptides as controls for chemical and enzymatic reactions, no polypeptide is available that is suitable for a wide variety of cleavages or reactions. Furthermore, because proteins contain many cleavage sites, use of proteins to monitor these reactions results in far too many fragments, which yield complex chromatograms. Thus, monitoring these reactions by use of a control protein unnecessarily complicates the subsequent analysis, making it difficult to determine the products and the reproducibility of the reaction. In addition, the commercial preparations of proteins or peptides often vary in purity and some residues may be modified in variable amounts in different preparations or from different manufacturers. Thus, there also exists a need for synthetic control peptides having amino acid sequences designed to have a limited but sufficient number of the appropriate amino acid residues so as to allow the monitoring of a wide variety of chemical and enzymatic reactions.

Throughout this application, various publications are referenced. The disclosures of these publications in their entireties are hereby incorporated by reference into this application in order to more fully describe the state of the art to which this invention pertains.

SUMMARY OF THE INVENTION

The present invention relates to novel peptides useful in the amino acid sequencing context and methods of their use. In particular, this invention relates to an amino acid sequencing internal standard peptide comprising unnatural amino acid residues that is capable of being sequenced simultaneously with an unknown peptide or protein without interfering with the analysis of the unknown peptide or protein. Information derived from the sequencing of the internal standard permits the monitoring of the sequencer performance during the sequencing of an unknown, including the determination of repetitive yield, lag and N-terminal blockage, as well as allowing for detection of and discrimination between a blank cycle caused by a missed injection and a blank cycle caused by faulty delivery of chemicals during the sequencer reactions.

The internal standard comprises a peptide consisting essentially of unnatural amino acid residues, which has an amino acid sequence containing at least two different unnatural amino acid residues such that the retention time for each unnatural amino acid residue following derivatization in an amino acid sequencer is distinct from the corresponding retention times for natural amino acid residues. Two consecutive occurrences of at least one unnatural amino acid residue in the amino acid sequence are separated by at least one differing amino acid residue to allow determination of repetitive yield and at least 70% of the unnatural amino acid residues are positioned in the amino acid sequence so as to be separated by at least one differing amino acid residue to allow determination of lag.

Further, this invention relates to synthetic control peptides comprising natural amino acid residues that are designed for use in monitoring the proper operation of amino acid sequencers and for confirming that the system properly identifies all the common amino acid residues. In one embodiment, pairs of these control peptides may be sequenced simultaneously without data interference between each other or β-lactoglobulin, a commonly used protein sequencing standard, for enough cycles to obtain data for common or uncommon amino acids, for easy or difficult to measure amino acids, and for initial and repetitive yields based upon only the stable and reliable PTH-derivatives. In this manner, the control peptides provide a means to optimize the sequencer for peptide sequencing or to simultaneously compare the sequencer performance and optimization conditions for both proteins and peptides.

These synthetic control peptides can also be used as controls in a wide variety of chemical and enzymatic reactions. Specific amino acid residues are strategically located to provide cleavage sites for various amino acid cleavage reactants. Thus, the control peptides can be reacted with the cleavage reactants and the resulting fragments can be analyzed to qualitatively and quantitatively assess the occurrence, identity and extent of cleavage reactions.

The control peptides of this invention comprise from about 3 to about 100 natural amino acid residues and are designed to have 2 or more uncommon or difficult to measure residues within 15 amino acid residues from the N-terminus of the peptide as well as at least 4 different common amino acids within 15 amino acid residues from the N-terminus of the peptide.

DESCRIPTION OF THE FIGURES

FIG. 7 indicates preferred pairs of residues used to calculate repetitive yield and difficult amino acids within 10 residues of the N-terminus for the control peptides given by SEQ ID NO:3 and SEQ ID NO:4;

FIGS. 9 and 10 show examples of the theoretical results obtained from the reaction of some commonly employed chemical and enzymatic amino acid cleavage reactants with the control peptides having the sequences shown in SEQ ID NO:3 and SEQ ID NO:4, respectively.

DETAILED DESCRIPTION OF THE INVENTION

As used herein, the term "natural amino acid" or "natural amino acid residue" refers to naturally occurring amino acids or residues which typically occur in proteins, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. The term "unnatural amino acid" or "unnatural amino acid residue" refers to either naturally occurring amino acids or residues which typically do not occur in proteins or non-naturally occurring amino acids or residues, including both the D- and L-isomers, so long as the non-naturally occurring amino acid residues can be sequenced similarly to residues found in proteins or peptides. Many different unnatural amino acids exist; examples of unnatural amino acids include, but are not limited to, α-aminobutyric acid, norleucine, norvaline and ornithine.

As used herein, the term "uncommon amino acid" or "uncommon amino acid residue" refers to natural amino acids or residues which do not occur frequently or occur only moderately frequently in protein, such as cysteine, tryptophan, and histidine. Conversely, "common amino acids" or "common amino acid residues" refer to natural amino acids or residues which occur relatively frequently in protein. An amino acid or amino acid residue is "difficult to measure" if the sequencing procedures produce a derivative of the residue that is reactive and/or unstable or difficult to extract from the sequencing support or varies in rentention time due to slight changes in the HPLC buffers, which may change as they age. Examples of difficult to measure residues include serine, threonine, histidine, arginine, cysteine, and tryptophan.

The term "amino acid cleavage reactant" refers to a reactant that is capable of cleaving a protein or peptide predominately at a specific residue or at a specific sequence in the amino acid sequence based upon the identity of the amino acid residues at the location. For instance, the amino acid cleavage reactant trypsin is capable of cleaving a protein or peptide at positions in the amino acid sequence immediately following a lysine residue or an arginine residue, considering the sequence as ranging from the N-terminus to the C-terminus. Other examples of amino acid cleavage reactants include, but are not limited to Endoproteinase Asn-C, Endoproteinase Lys-C, Endoproteinase Arg-C, Endoproteinase Glu-C and Endoproteinase Asp-N, which can be obtained from Mannheim Boehringer Biochemica (Indianapolis, Ind.) and BNPS-skatole, trypsin, cyanogen bromide, V8-E-AB (V8 protease which cleaves E in ammonium bicarbonate), V8-DE-PO$^4$ (V8 protease specific for D and E in phosphate buffer), formic acid and acetic acid.

INTERNAL STANDARD PEPTIDES

Figure 1:
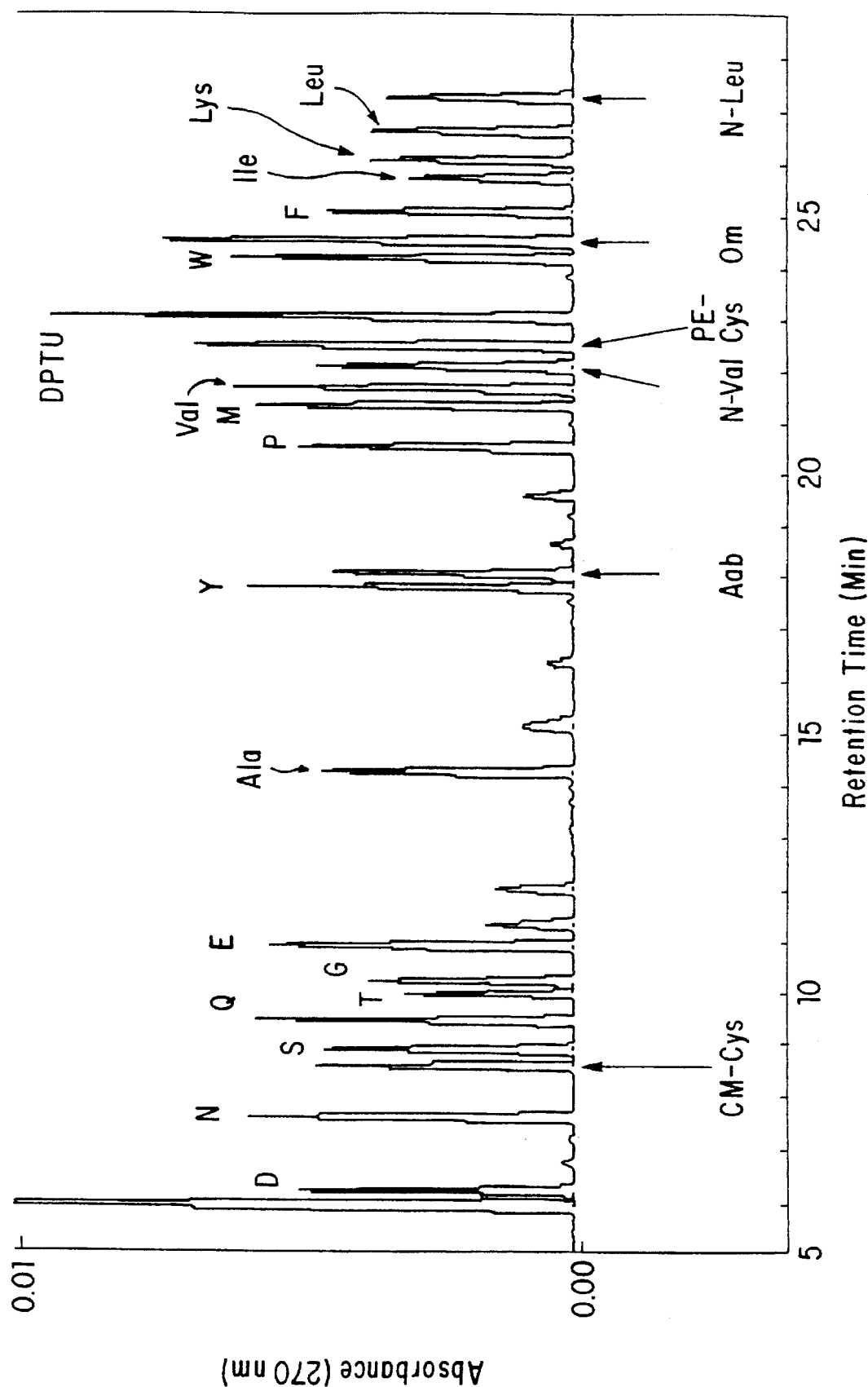
FIG. 1 presents an HPLC chromatogram showing the retention times for the PTH derivatives of the following amino acids: D (aspartic acid), N (asparagine), CM-Cys (carboxymethylcycsteine), S (serine), Q (glutamine), T (threonine), G (glycine), E (glutamic acid), A (alanine), Y (tyrosine), Aab (α-aminobutyric acid), P (proline), M (methionine), V (valine), Nval (norvaline), PE-Cys (pyridylethylcysteine), DPTU (N,N'-diphenylthiourea), W (tryptophan), Orn (ornithine), F (phenylalanine), Ile (isoleucine), Lys (lysine), Leu (leucine) and N-Leu (norleucine)

This invention provides for a synthetic, non-interfering internal standard for amino acid sequencing comprising a peptide consisting essentially of unnatural amino acid residues selected such that the retention time for each unnatural amino acid residue following derivatization in an amino acid sequencer is distinct, preferably baseline resolved, from the retention times for corresponding natural amino acid residues. It is important that the peptide does not contain any natural amino acid residues because their presence could interfere with the analysis of the unknown sample. Further, the elution times for the derivatives, such as PTH-derivatives, of the selected unnatural amino acid residues are within the times normally seen for the corresponding natural amino acid derivatives formed using the same sequencer reactions. Because the internal standard peptide can be sequenced simultaneously with an unknown peptide or protein sample in an amino acid sequencer without interfering with the analysis of the unknown, the internal standard provides a means to monitor the sequencer performance during the sequencing of the unknown. FIG. 1 depicts a typical HPLC chromatogram showing the rentention times for PTH-derivatives of natural amino acids and some unnatural amino acids. The elution times for the unnatural amino acids are adequately different from those of the natural PTH-amino acids.

The amino acid sequence of the internal standard peptide is designed such that multiple occurrences of at least one particular residue that yields a stable and reliable PTH-derivative are separated by at least one, preferably two or more, other residues so as to allow calculation of initial and repetitive yields for that residue.

Furthermore, the amino acid sequence of the internal standard peptide is also designed such that at least 70%, preferably 80%, more preferably 100% of the multiple occurrences of any particular residue are separated by at least one, preferably two or more, other residues. In the N-terminal portion of the peptide, it is preferred that 100% of the multiple occurrences of any particular residue are separated by at least one, preferably two or more, other residues. In this manner, the lag caused by the processing of the particular residue in an earlier amino acid sequencer cycle will be minimized or eliminated during the subsequent processing of the same kind of residue in a later cycle. Because positioning of charged residues near the C-terminus of the peptide may promote adherence of the internal standard to the sample support in the sequencer, it may be useful to position residues, such as ornithine, in the C-terminus region such that they are not separated by other residues. However, a single ornithine at the C-terminus would mimic the type of peptide obtained by digestion with trypsin and would allow for sequencing to the end of the peptide.

Although the number of residues contained in a single peptide chain of the internal standard could be any number 2 or larger, cost and time considerations will generally limit the peptide size to between 2 and 100 residues, preferably between 5 and 60 residues, most preferably between 10 and 40 residues. Typically, the longer the peptide is, the less likely it is to "wash out" of the amino acid sequencer. Thus, a higher molecular weight internal standard tends to behave more similarly to a protein, including having an increased repetitive yield, compared to lower molecular weight peptides. Decreasing the length of the internal standard tends to have the opposite effect. Thus, peptides of varying lengths can be synthesized to provide internal standards capable of more realistically monitoring the effect of the amino acid sequencing process on similarly sized peptides.

Furthermore, the identity and location of hydrophobic and hydrophilic amino acid residues in the peptide can be designed to avoid solubility problems and difficulty during the HPLC purification. For instance, because of the hydrophobicity of norleucine residues, a peptide containing too many of these residues can be difficult to dissolve and purify by HPLC. Thus, an excess of norleucine residues in the internal standard should be avoided Conversely, more hydrophilic residues, such as ornithine, aid in solubility and subsequent purification.

Incorporation of residues in the peptide that cause problems in the synthesis or deprotection of the peptide should be avoided to circumvent or decrease the problem of low yields for the final product. Furthermore, using an Applied Biosystems, Inc. (ABI) (Foster City, Calif.) 475A sequencer modified with bottle and regulator updates with an on-line Model 120A PTH-amino acid analyzer, PTH-β-cyclohexylalanine did not have an HPLC retention time unique from the corresponding PTH-common amino acids, and should not be incorporated in internal standard peptides designed to function in this system. If desired, more expensive unnatural amino acids, such as L-2,4-diaminobutyric acid and L-2,3-diaminopropionic acid, can be avoided.

Using the above guidelines, synthesis of various internal standard peptides from synthetic unnatural amino acids can be performed using standard procedures, such as t-boc chemistry. However, the use of FastMoc™ chemistry is preferred because cleavage of the peptide from the resin and deprotection is simpler than the HF needed for synthesis using t-boc chemistry. In short, internal standard peptides can be synthesized by solid phase synthesis using an ABI Model 430A Peptide Synthesizer. The FastMoc™ chemistry approach (0.25 mmolar scale) can be utilized essentially as described in "FastMoc™ Chemistry: HBTU Activation in Peptide Synthesis on the Model 430A", Applied Biosystems User Bulletin Issue No. 32 (November 1990) and the synthesizer can be controlled by the HBTU.25 Run File of the ABI FastMoc™ software (version 1.4). Of course, other run files and synthesizers may be successfully used.

The internal standard may further comprise a charged substrate or solid support attached to or near the C-terminus of the amino acid sequence so as to minimize wash out of the internal standard from the amino acid sequencer. By connecting the peptide to such materials, or by synthesizing them onto materials, the effective molecular weight of the internal standard increases, leading to effects similar to increasing the molecular weight. For instance, suitable substrates include but are not limited to the following substrates: a peptide comprising at least one charged unnatural amino acid residue, a peptide comprising at least one charged natural amino acid residue and peptides comprising a mixture of charged unnatural and charged natural amino acid residues. Furthermore, the internal standard peptide can be synthesized onto a multiple antigenic peptide resin, such as a t-boc MAP resin, Fmoc MAP Resin 4-Branch or Fmoc MAP Resin 8-Branch (obtained, for example, from ABI). Additionally, the peptide can be covalently attached to other solid supports, similar to those used in solid phase sequencing.

The internal standard of this invention can be used to monitor the performance of the amino acid sequencer during the sequencing of an unknown peptide or protein. A small amount, preferably close to the amount estimated for the unknown, of the internal standard is placed on the glass filter disc of an amino acid sequencer (any manufacturer for this type of instrument). The unknown sample to be sequenced is also placed on this filter and the experiment is started. The sequencer automatically repeats a series of reactions on both the unknown sample and the internal standard. The general steps are as follows: couple the N-terminal amino acids with phenylisothiocyanate; cleave the amino acids to yield the PTC derivatives, convert the PTCs to PTH derivatives, and inject the two PTHs into an HPLC system. The HPLC unit then separates the PTH derivatives, which are identified by comparing the retention times with those of known standards. Each cycle of the sequencer result should give the expected synthetic PTH amino acid for the internal standard in an amount that is reasonable and reproducible when the equipment is operating normally. Furthermore, each cycle of the sequencer can be checked to verify that no more than reasonably expected lag for the synthetic unnatural PTH amino acids is present.

An initial yield can be calculated for the internal standard by comparing the quantity of the synthetic amino acid that is obtained in cycle 1 (PTH-Orn for internal standards defined by SEQ ID NO:1 and SEQ ID NO:2) with the amount of the peptide that was added originally. This initial yield should normally be about 40–60% for a sequencer that is functioning properly.

Several repetitive yields from the internal standard can be calculated during the actual sequencing of the unknown sample. The repetitive yield values are extremely important in determining the operation of the equipment during a run. For instance, the Applied Biosystems sequencer is guaranteed in service maintenance contracts to have a repetitive yield of at least 92%. This value is tested in an experiment using the ABI protein standard, β-lactoglobulin. However, a good repetitive yield during the sequencing of this protein does not insure that the equipment will work properly in the next experiment. For instance, any of the many (100s) of valves, lines, and circuits present in the sequencer could develop problems or leaks at any time. Also, approximately 15 different reagents are being continually consumed and replaced. Occasionally, some bottles of these chemicals are found to give poor results, but, prior to this invention, was not normally realized until several unknown samples had been analyzed. However, the internal standard of this invention allows the measurement of repetitive yield during the sequencing of the unknown. Thus, sequencer errors can be determined as they occur, preventing the waste of time and, frequently, unnecessary loss of unknown sample. The repetitive yield (RY) is determined by the following formula:

$$RY = \left[\frac{\text{pmoles } PTH \text{ in cycle } Y}{\text{pmoles } PTH \text{ in cycle } X}\right]^{[1/(Y \text{ residue } \#-X \text{ residue } \#)]}$$

Figure 2:
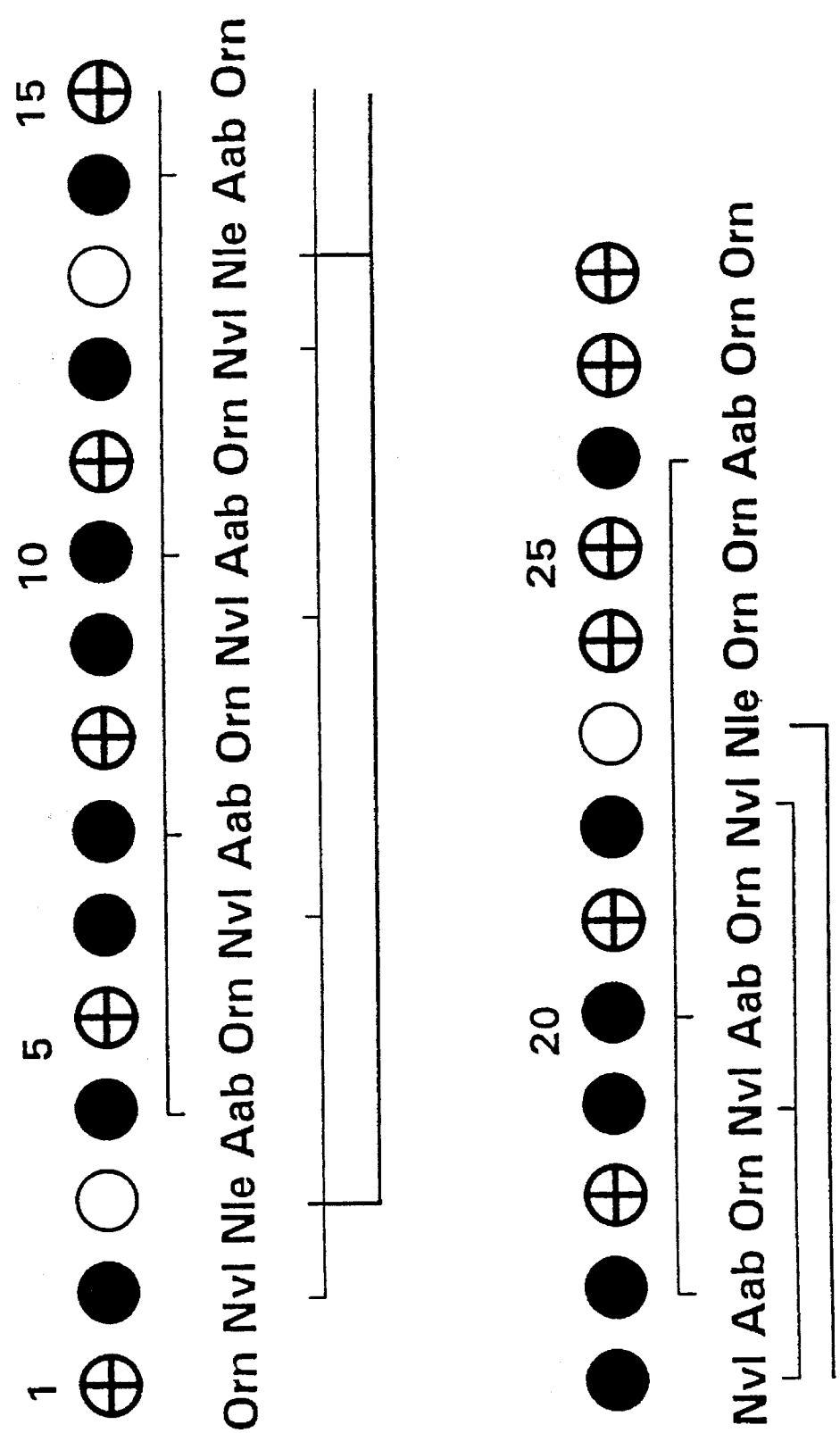
FIG. 2 illustrates example pairs of residues, indicated by the lines drawn between the individual amino acids, from which repetitive yield values can be determined when sequencing SEQ ID NO:1.

FIG. 2 illustrates some of the various possible pairs of residues from which repetitive yield values can be calculated when sequencing the internal standard SEQ ID NO:1 simultaneously with an unknown peptide or protein. These pairs are indicated by the lines drawn between the individual amino acids. For clarity, lines between various ornithine residues were omitted; ornithine residues can be used to determine repetitive yield.

The internal standard of this invention is a more realistic standard for the sequencing of peptides than a protein internal standard because a protein standard is not as sensitive to being washed from the sample support as the peptide sample being sequenced. Optimizing the sequencer flow rates, reaction times, etc. for the internal standard would also optimize the machine for internal peptides obtained enzyme digests or chemical cleavages. Furthermore, optimizing the sequencer for the internal standard would also set the machine correctly for the sequencing of proteins. Lags can be easily detected for the internal standard because the amino acid residues are separated by at least one other residue.

The internal standard is capable of detecting errors attributable to the unknown, such as N-terminal blockage in the unknown protein or peptide. That is, cycles which do not produce HPLC peaks for the unknown but yield the expected peaks for the internal standard allow the operator to conclude that the instrument is functioning properly and the lack of peaks lies with the sample. Furthermore, the internal standard can distinguish between a missed injection and a blank cycle caused by faulty delivery of chemicals during the sequencer reactions. That is, the internal standard will yield at the next cycle either the residue expected following an injection problem or the one that was expected in the missed cycle. These results would indicate that the previous amino acid was not injected or that the chemical reactions did not occur during that cycle, respectively. For example, if a blank occurred at cycle 3 of the internal standard defined by SEQ ID NO:1, the next residue would be expected to be the following depending upon the problem:

|  | 1 | 2 | 3 | 4 |
|---|---|---|---|---|
| correct sequence | orn | nvl | NLE | aab |
| missed injection | orn | nvl | — | aab |
| missed chemicals | orn | nvl | — | NLE |

Preferably, the internal standard peptide either contains at least three different unnatural amino acids or does not exist solely as alternating amino acid residues so as to be able to differentiate between missed injection errors and malfunctioning chemical processing errors when two adjacent cycles are blank. For example, a sequence having the pattern ABABABABAB would not differentiate between these errors. However, if a third different residue is present in the sequence following the blank cycles, such as in the pattern ABABABABAC, or if the pattern is not solely alternating, such as ABABABABAA, the internal standard peptide would be able to differentiate between these types of errors.

An additional advantage of the internal standard peptide of this invention is that the PTH derivatives formed during sequencing may act as carriers for the PTH residues formed from the unknown sample. It would be possible to improve the sequence results of, say, 1 pmol of an unknown by adding 50 pmol of the internal standard. Additionally, the internal standard peptide could act as a carrier to prevent commonly observed loss of unknown sample peptides during their purification for sequencing. For example, 200 pmol of the standard could be added to tubes used to collect peptides during HPLC purifications. The presence of the standard would not interfere with the subsequent sequencing analysis.

The present internal standard is more particularly described in the following examples which are intended as illustrative only since numerous modifications and variations therein will be apparent to those skilled in the art.

EXAMPLE 1

The peptide whose sequence is given by SEQ ID NO:1 was synthesized by solid phase synthesis using an ABI Model 430A Peptide Synthesizer and the FastMoc™ chemistry as described above. The following synthetic amino acids, with the indicated protecting groups, were use for the synthesis: 9-fluorenylmethoxycarbonyl(Fmoc)-L-norleucine; Fmoc-norvaline; Fmoc-ornithine (t-butyloxcarbonyl) and Fmoc-L-α-aminobutyric acid. The first amino acid was attached to the p-hydroxy-methylphenoxymethyl-polystyrene (HMP) resin by the synthesizer (cycles rfmcl1d, cfmc 11d, and afmc 11d) and then capped with benzoic anhydride (cycles rfmcl1, cfmc 11, and afmc 11). The other residues were added using the HBTU.25 Run File, as discussed above (cycles RHBTU.25, CHBTU.25, and AHBTU25X).

The N-terminal Fmoc group was automatically removed by the Synthesizer using the RNH2.25, CEND, and AEND cycles. The internal standard peptide was then cleaved from the resin and simultaneously deprotected by incubating 0.2 g of the peptide-resin for 1.5 h in a solution composed of 0.75 g crystalline phenol, 0.25 ml 1,2-ethanedithiol, 0.5 ml thioanisole, 0.5 ml deionized water, and 10 ml trifluoroacetic acid. The peptide was then precipitated in ethyl ether, filtered, and washed on a fritted glass funnel. This procedure is described in the ABI booklet "Introduction to Cleavage Techniques-Strategies in Peptide Synthesis."

The peptide was purified by dissolving it in 0.1% TFA and purified by high performance liquid chromatography (HPLC) utilizing an Aquapore RP300 column equilibrated with 0.1% TFA. The sample was then eluted with a 7.5 min linear gradient of 0% to 52% acetonitrile containing 0.07% TFA. The peptide whose sequence is given by SEQ ID NO:2 was synthesized similarly.

EXAMPLE 2

Figure 3:
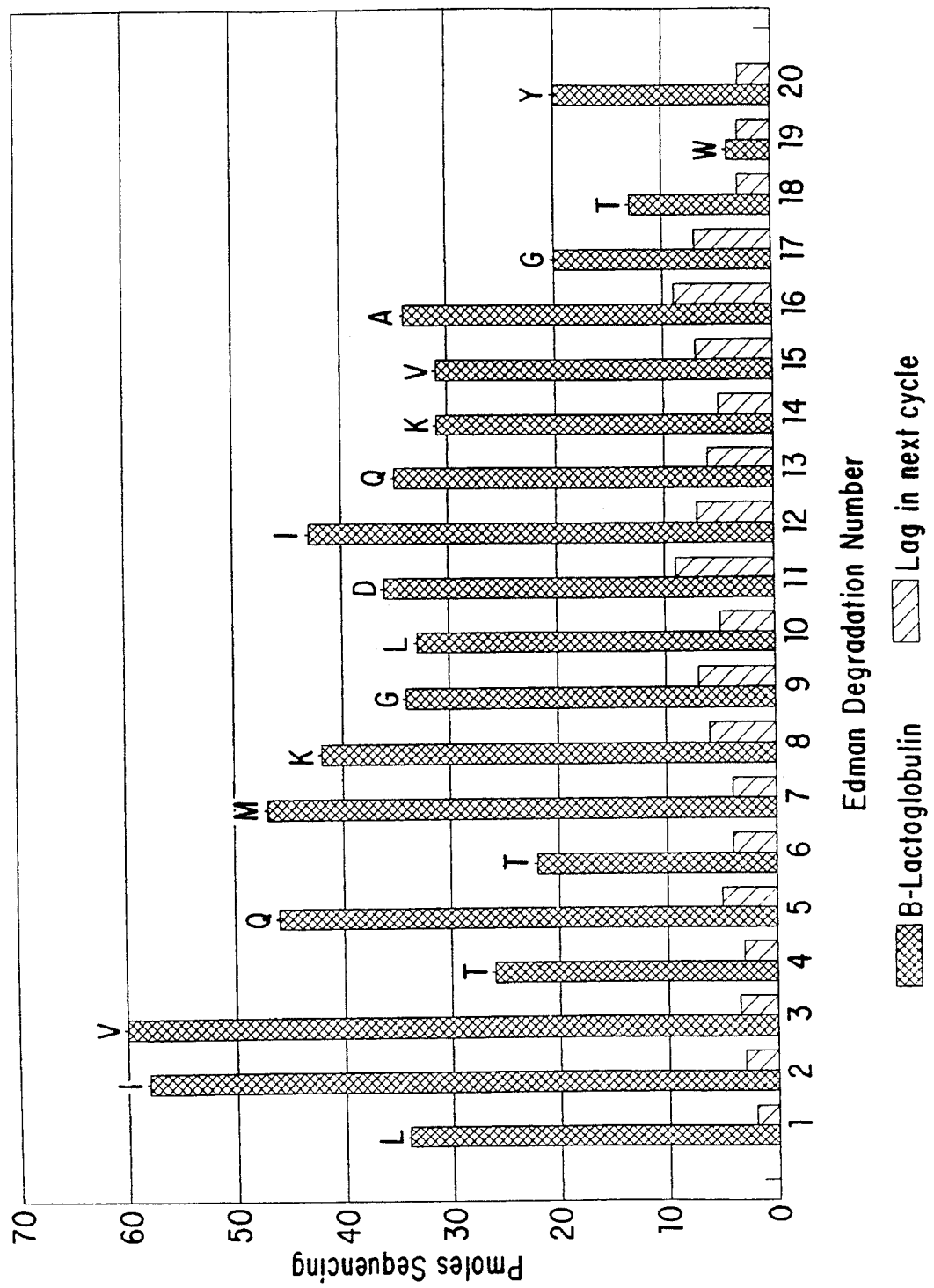
FIG. 3 shows a bar graph depicting the cycle yields and repetitive yields for the β-lactoglobulin sequence with lag obtained from the simultaneous sequencing of β-lactoglobulin and SEQ ID NO:1.
Figure 4:
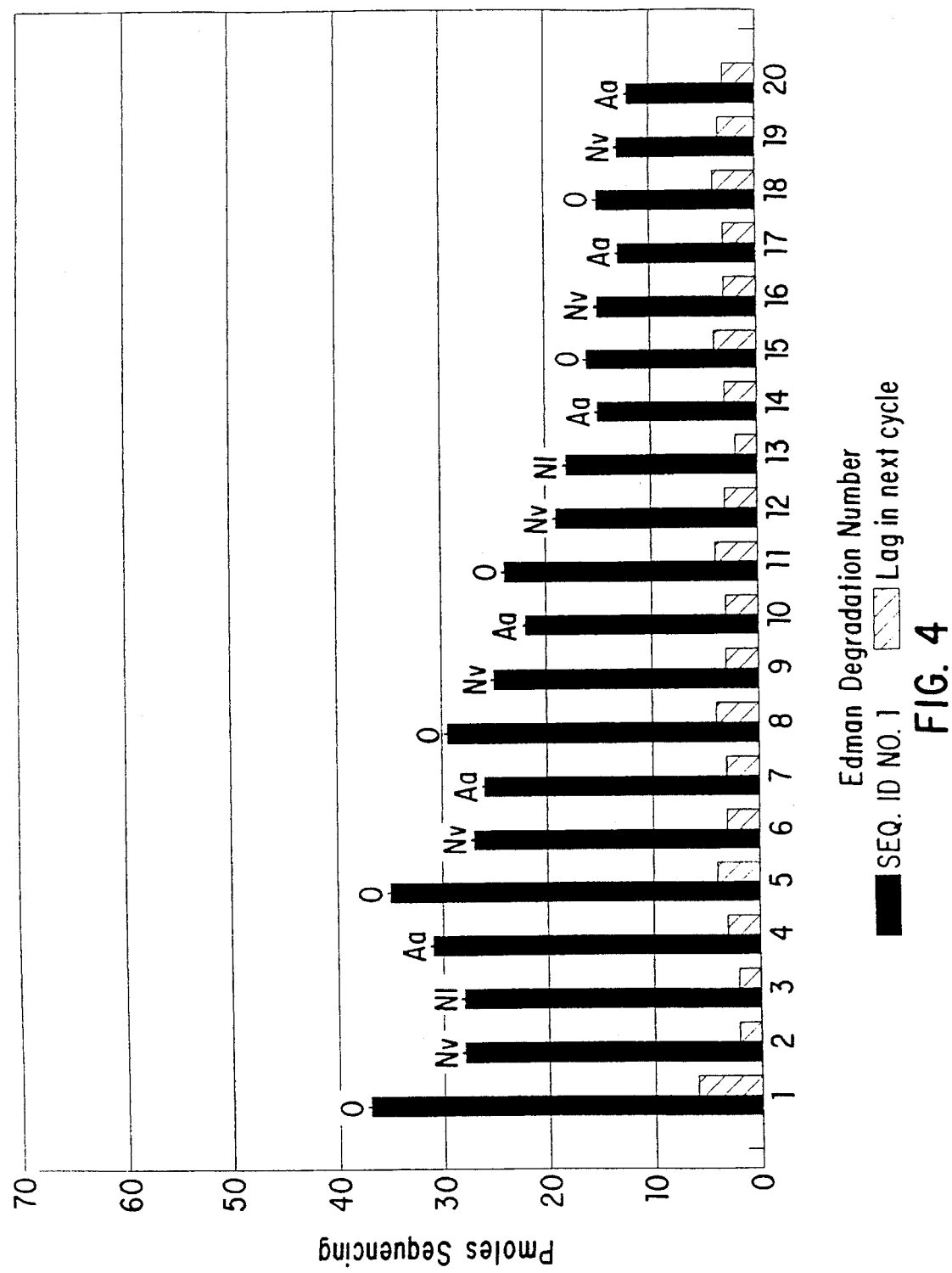
FIG. 4 shows a bar graph depicting the cycle yields and repetitive yields for the internal standard SEQ ID NO:1 with lag obtained from the simultaneous sequencing of β-lactoglobulin and SEQ ID NO:1.
Figure 5:
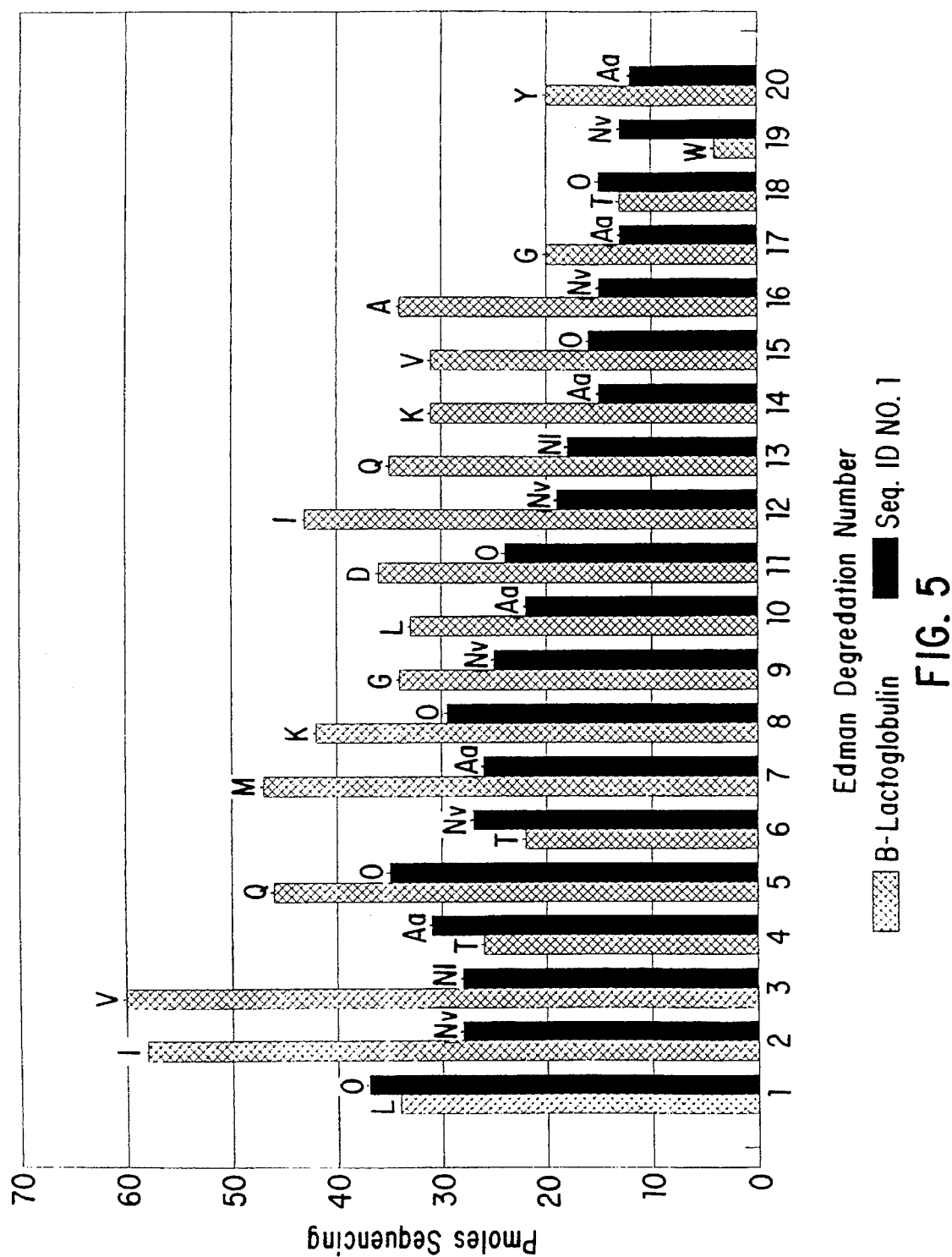
FIG. 5 shows a bar graph depicting the cycle sequence results for β-lactoglobulin and the internal standard SEQ ID NO:1 obtained from the simultaneous sequencing of β-lactoglobulin and SEQ ID NO:1.

The protein β-lactoglobulin (100 pmol) was sequenced simultaneously with SEQ ID NO:1 (100 pmol) on an ABI 475A sequencer modified with bottle and regulator updates and equipped with an on-line Model 120A PTH-amino acid analyzer. Porton Peptide supports were utilized with the normal cartridge. FIGS. 3–5, show a bar graph depicting the cycle yields and repetitive yields for the β-lactoglobulin sequence with lag, the cycle yields and repetitive yields for the internal standard (SEQ ID NO:1) with lag, and the sequence results for β-lactoglobulin and the internal standard (SEQ ID NO:1), respectively.

Figure 6A:
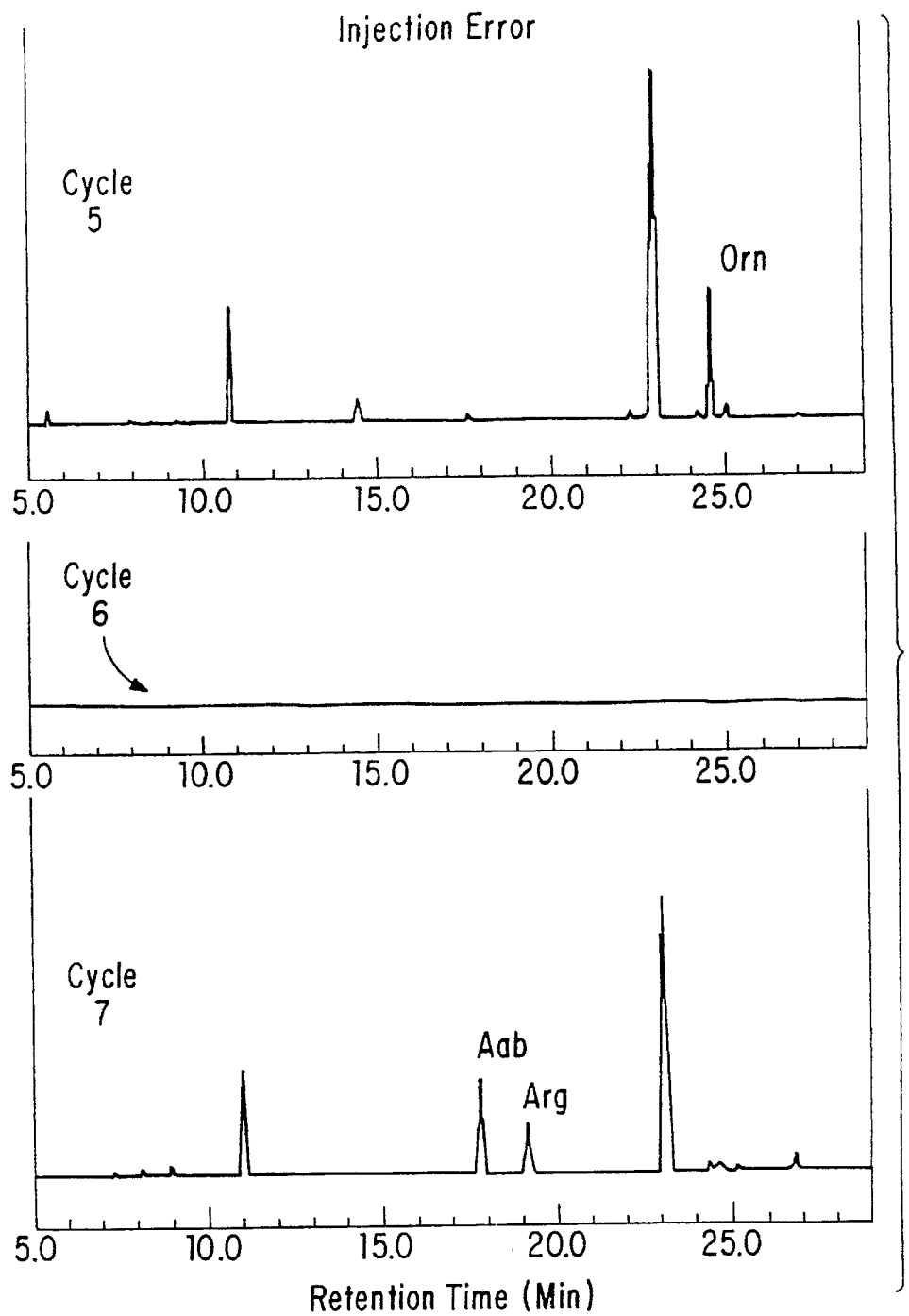
FIG. 6 shows three cycles each from two sets of HPLC chromatograms obtained from the sequencing of SEQ ID NO:1 with unknown sample to illustrate how an injection error is distinguished from a chemistry error during the sequencing of an unknown.
Figure 6B:
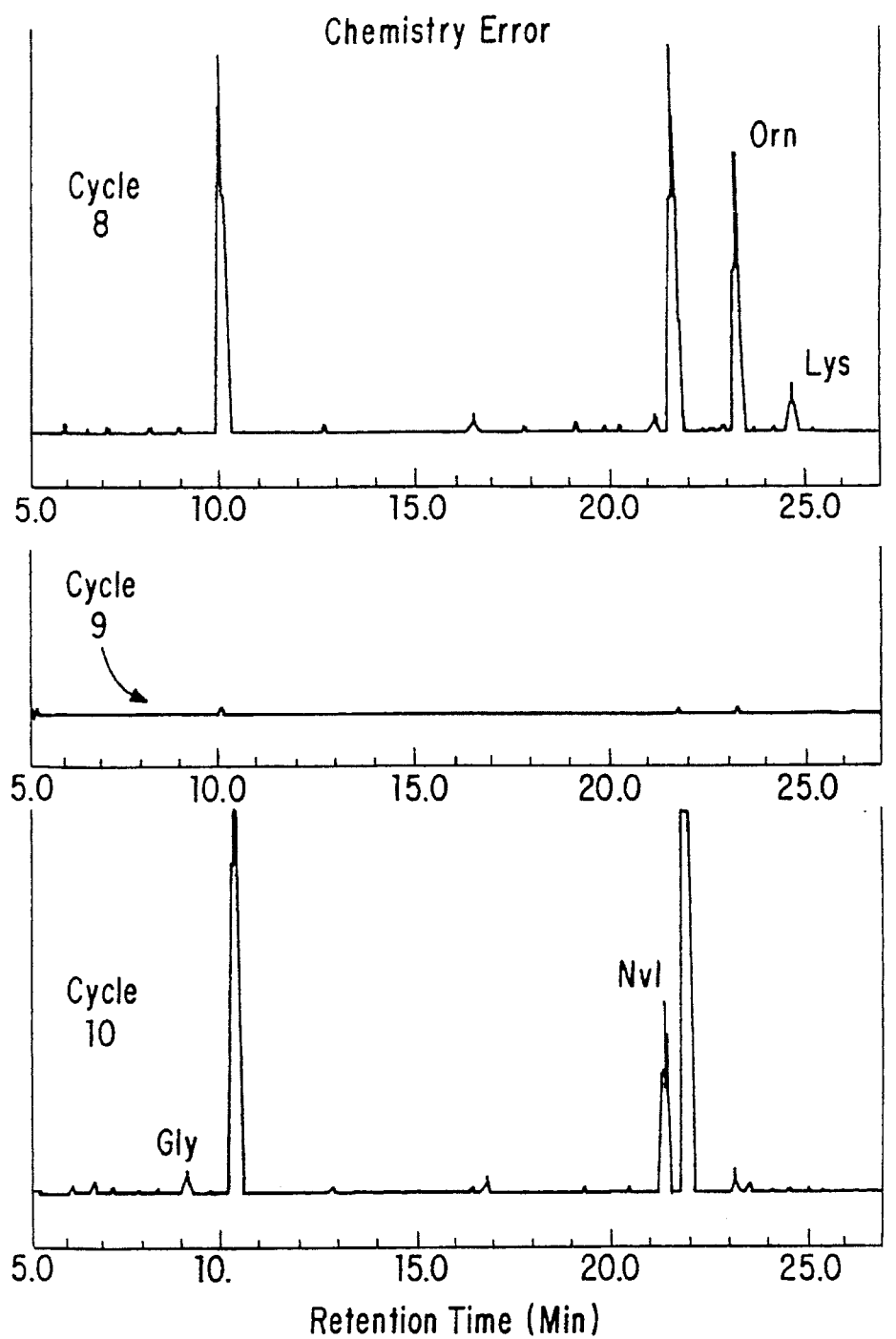

In the course of using SEQ ID NO:1 as an internal standard when sequencing various unknown proteins and peptides, various injection and chemistry errors were detected. FIG. 6 shows three cycles from two sets of HPLC chromatograms obtained from the sequencing of SEQ ID NO:1 with unknown samples to illustrate how an injection error can be distinguished from a chemistry error. In both sets, the cause behind the blank cycles was clearly delineated.

CONTROL PEPTIDES

This invention also provides novel synthetic control peptides designed for use in monitoring the proper operation of amino acid sequencers that have amino acid sequences containing from about 3 to about 100 natural amino acid residues. These control peptides, which preferably can be sequenced in an amino acid sequencer without data interference from the protein standard β-lactoglobulin, are constructed to provide sequencing information quickly to the operator so as to allow efficient optimization of the sequencer, particularly with respect to the sequencing of unknown peptides. In particular, the control peptides are designed to provide sequencing information regarding uncommon and difficult to measure amino acids as well as many, preferably all, common amino acids during the early cycles of the amino acid sequencer. Further, compositions containing at least two of these control peptides are specifically designed to provide this sequencing information without data interference with each other or, preferably, with β-lactoglobulin.

In particular, the amino acid sequences for these control peptides are constructed so as to place at least some uncommon and/or difficult to measure amino acid residues within 15 amino acid residues from the N-termini of the peptides. Preferably, the amino acid sequences have at least 2 uncommon or difficult to measure residues, such as a cysteine residue, a tryptophan residue, a serine residue, a threonine residue, a histidine residue, an arginine residue or a methionine residue, located within 15 amino acid residues, more preferably within 10 amino acid residues, from the N-terminus of the peptide. Furthermore, the remaining residues are selected so as to provide a wide variety of common amino acids, preferably having at least 4, more preferably at least 7, different common amino acids located within 15 amino acid residues of the N-terminus. Preferred peptides are constructed such that at least one residue, more preferably two different residues, which possesses a stable PTH-derivative is repeated at least one time, but not immediately adjacent the first occurrence, within 15 amino acid residues of the N-terminus to allow calculation of repetitive yield. Useful control peptides include, but are not limited to, peptides having the sequences given in SEQ ID NO:3, SEQ ID NO:4, SEQ ID NO:5 and SEQ ID NO:6.

Additionally, the control peptides preferably are designed so as to not interfere with the simultaneous sequencing of β-lactoglobulin. In this manner, the control peptides can be sequenced simultaneously with β-lactoglobulin so as to provide information comparing the sequencing of the peptides with this ABI protein standard. To be non-infereing, each control peptide amino acid residue at a particular residue location number differs from the β-lactoglobulin amino acid residue having a residue location number ranging at least from the particular residue location number minus 1 to the particular residue location number plus 1. In this context, the residue location number for either the control peptide or for β-lactoglobulin is measured from the N-terminus of the control peptide or β-lactoglobulin, respectively. That is, the amino acid residue at, for instance, residue location number 10 of the control peptide will be different from the amino acid residues located at residue location numbers 9–11 of β-lactoglobulin. In this manner, lag from residues that originated from the control peptide will not interfere with residues that originated from β-lactoglobulin, or vice versa, because at least one sequencer cycle will occur following the sequencing of a particular residue before that particular residue is sequenced again, whether it originated from the control peptide or β-lactoglobulin. Useful non-interfering control peptides include, but are not limited to, peptides having the sequences given in SEQ ID NO:3, SEQ ID NO:4 and SEQ ID NO:6.

Compositions containing at least two of the control peptides discussed above are particularly useful for monitoring the proper operation of amino acid sequencers because they are capable of more quickly confirming whether the system properly identifies all the pertinent amino acid residues. That is, the control peptides selected for use in the composition can be sequenced simultaneously without data interference with each other. Further, the peptides can be synthesized to have complementary properties such that the amino acid residues located within 15 residues of the N-terminus of one peptide are generally different from those located in the corresponding region on any other peptide. In this manner, it is possible to formulate a composition which, when subjected to sequencing, provides information regarding many, preferably at least five, uncommon or difficult to measure amino acids, such as cysteine, tryptophan, serine, threonine, histidine, and arginine, within the first 15 cycles, preferably the first 10 cycles, of the sequencer. Additionally, the control peptides can be designed to complement each other with respect to providing information regarding the common amino acids, preferably having at least 8, preferably at least 10, common amino acids located within the first 15 amino acid residues from the N-termini of the peptides. FIG. 6 shows the amino acid structure for SEQ ID NO:3 and SEQ ID NO:4 in addition to labeling the difficult amino acids located within 10 residues of the N-termini.

As discussed above, preferably none of the peptides in the composition interfere with β-lactoglobulin; furthermore, to allow measurement of lag and repetitive yield, none of the peptides in the composition should interfere with each other. That is, each control peptide amino acid residue at a particular residue location number differs from the amino acid residue for any other control peptide having a residue location number ranging from the particular residue location number minus 1 to the particular residue location number plus 1. Useful compositions containing at least two control peptides include, but are not limited to, compositions comprising the peptides having the sequences given in SEQ ID NO:3 and SEQ ID NO:4 or SEQ ID NO:5 and SEQ ID NO:6.

Small amounts, similar to amounts used to sequence unknowns, of the control peptide or a composition containing at least two control peptides, preferably containing approximately equal amounts of the peptides, can be placed on the glass filter disc of an amino acid sequencer. If desired, β-lactoglobulin, preferably about 100 pmol, may also be placed on this filter. The sequencer automatically repeats a series of reactions as described above for the internal standard peptide. Each cycle of the sequencer result should give the expected synthetic PTH amino acids in an amount that is reasonable and reproducible when the equipment is operating normally. If the expected results are not achieved, adjustments to the parameters controlling the amino acid sequencer, such as changing the flow rates of the various reactants, washing times, drying times, injection volumes, etc., can be made to optimize the amino acid sequencer for peptide sequencing.

As discussed above, the synthetic control peptides of this invention are capable of assessing amino acid sequencer performance by allowing the measurement of repetitive yield, which is extremely important in determining the operation of the sequencer. Knowledge regarding repetitive yield aids in the optimization process, which in turn improves the chances for the proper identification of difficult amino acids. Preferably, the repetitive yield should be determined from multiple occurrences of a residue which derivitizes to a PTH-amino acid that is both stable and extracts well.

Repetitive yield values are commonly measured and averaged by sequencing the protein β-lactoglobulin. One disadvantage of using this protein, however, is that the sequencer is only optimized for high molecular weight components and does not insure that the equipment will work properly for relatively small peptides. For example, excessive flow rates or washing times do not increase the amount of sample loss as much for β-lactoglobulin as for low molecular weight peptides, such as the small peptides that are normally obtained during internal sequencing experiments. Thus, too much solvent flow could wash the peptide off the support long before the C-terminus is reached. By optimizing the sequencer using a control peptide of this invention, preferably a composition containing a mixture of the control peptides, most preferably simultaneously using a composition containing a mixture of the control peptides and β-lactoglobulin, it is possible to determine the optimization for both low and high molecular weight components. For instance, in a single 17 cycle experiment in which a composition containing a mixture of control peptides having the sequences of SEQ ID NO:3 and SEQ ID NO:4 is simultaneously sequenced with β-lactoglobulin, 7 and 3 good repetitive yield values, respectively, can be obtained. Additionally, this procedure provides for the determination of 3 initial yields.

The synthetic control peptides of this invention can also be used as controls in a wide variety of chemical and enzymatic reactions. Successful microsequence analyses of samples available in limited quantities, or purified by 1D or 2D-PAGE, require precise utilization of techniques and maximally efficient operation of all analytical systems. This is especially important when internal sequencing on this type of sample is performed. Therefore, it is imperative that chemical modification and cleavage reactions and enzymatic digests are periodically tested or done in parallel with the sample unknowns. This testing insures that the expected results are obtained or indicates where problems may exist.

The control peptides are designed so that specific amino acid residues are strategically placed within the amino acid sequences to provide cleavage sites for these reactions. Preferably, the control peptide contains amino acid patterns that are capable of reacting with at least 4, more preferably 5 or more amino acid cleavage reactants. The resulting fragments can then be analyzed to qualitatively and quantitatively assess that the desired cleavages occurred. For example, the cleavage products can be analyzed and purified by HPLC and then all peaks identified by amino acid sequencing. Future experiments using the same cleavage conditions would also check the reproducibility of peptide retention times observed by HPLC analysis.

Thus, peptide or protein cleavage reactions can be monitored by reacting a control peptide of this invention having at least one specific amino acid cleavage site with an amino acid cleavage reactant capable of cleaving a protein or peptide at the specific amino acid cleavage site; analyzing the cleavage products to determine the identity and quantity of the cleavage products; and comparing the identity and quantity of the cleavage products to the expected yield for the reaction between the control peptide and the amino acid cleavage reactant to monitor the peptide or protein cleavage reaction. Preferred control peptides include SEQ ID NO:3, SEQ ID NO:4, SEQ ID NO:5 and SEQ ID NO:6. Examples of common amino acid cleavage reactants include, but are not limited to, Endoproteinase Asn-C, Endoproteinase Lys-C, Endoproteinase Arg-C, Endoproteinase Glu-C and Endoproteinase Asp-N, which can be obtained from Mannheim Boehringer Biochemica (Indianapolis, Ind.) and BNPS-skatole, trypsin, cyanogen bromide, V8-E-AB (V8 protease which cleaves E in ammonium bicarbonate), V8-DE-PO$^4$ (V8 protease specific for D and E in phosphate buffer), formic acid and acetic acid.

The present control standards are more particularly described in the following examples which are intended as illustrative only since numerous modifications and variations therein will be apparent to those skilled in the art.

EXAMPLE 3

The control peptides of this invention can be synthesized, cleaved and deprotected, and purified using the procedures outlined in Example 1 above for the synthesis of the internal standard peptide. The following synthetic amino acids, with the indicated protecting groups, can be used for the synthesis: Fmoc-L-alanine; Fmoc-L-arginine (Pmc); Fmoc-L-asparagine (Trt); Fmoc-L-aspartic acid (OtBu); Fmoc-L-cysteine (Trt); Fmoc-L-glutamine (Trt); Fmoc-L-glutamic acid (OtBu); Fmoc-L-glycine; Fmoc-L-histidine (Trt); Fmoc-L-isoleucine; Fmoc-L-leucine; Fmoc-L-lysine (Boc); Fmoc-L-methionine; Fmoc-L-phenylalanine; F-moc-proline; Fmoc-L-serine (tBu); Fmoc-L-threonine (tBu); Fmoc-L-tryptophan; Fmoc-L-tyrosine (tBu); and Fmoc-L-valine (protecting group abbreviations: Boc =t-butyloxycarbonyl; Otbu=tert-butyl ester; Pmc=2,2,5,7,8-pentamethyl-chroman-6-sulfonyl; tBu=tert-butyl; and Trt=trityl). Control peptides given by the sequences shown in SEQ ID NO:3, SEQ ID NO:4, SEQ ID NO:5 and SEQ ID NO:6 were synthesized in this manner.

EXAMPLE 4

Figure 8:
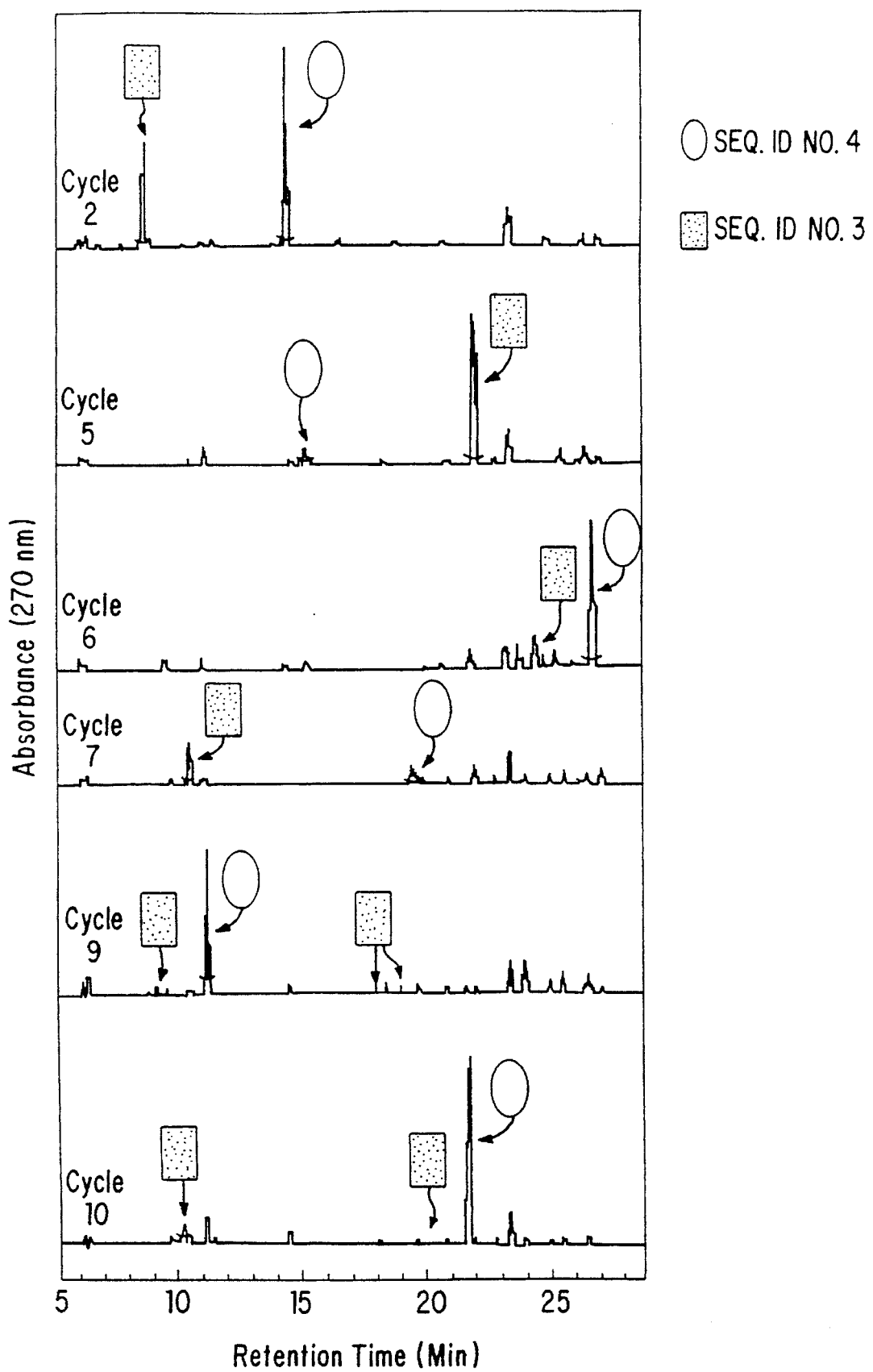
FIG. 8 shows the sequencing results from the simultaneous analysis of control peptides SEQ ID NO:3 and SEQ ID NO:4 for various sequencer cycles.

Control peptides SEQ ID NO:3 and SEQ ID NO:4 were simultaneously sequenced as were SEQ ID NO:5 and SEQ ID NO:6 to successfully verify that these pairs of peptides were noninterfering and were able to provide information regarding uncommon, difficult to measure and common amino acid. Various supports can be used such as Problot (particularly for transblotted samples or samples purified from 1D or 2D-PAGE experiments) or Porton Peptide filters (for samples purified by HPLC). FIG. 8 shows typical HPLC chromatographic results from cycles 2, 5, 6, 7, 9 and 10 of the simultaneous sequencing of SEQ ID NO:3 and SEQ ID NO:4, demonstrating the identification of difficult to measure or uncommon amino acids using these two control peptides.

EXAMPLE 5

Figure 11:
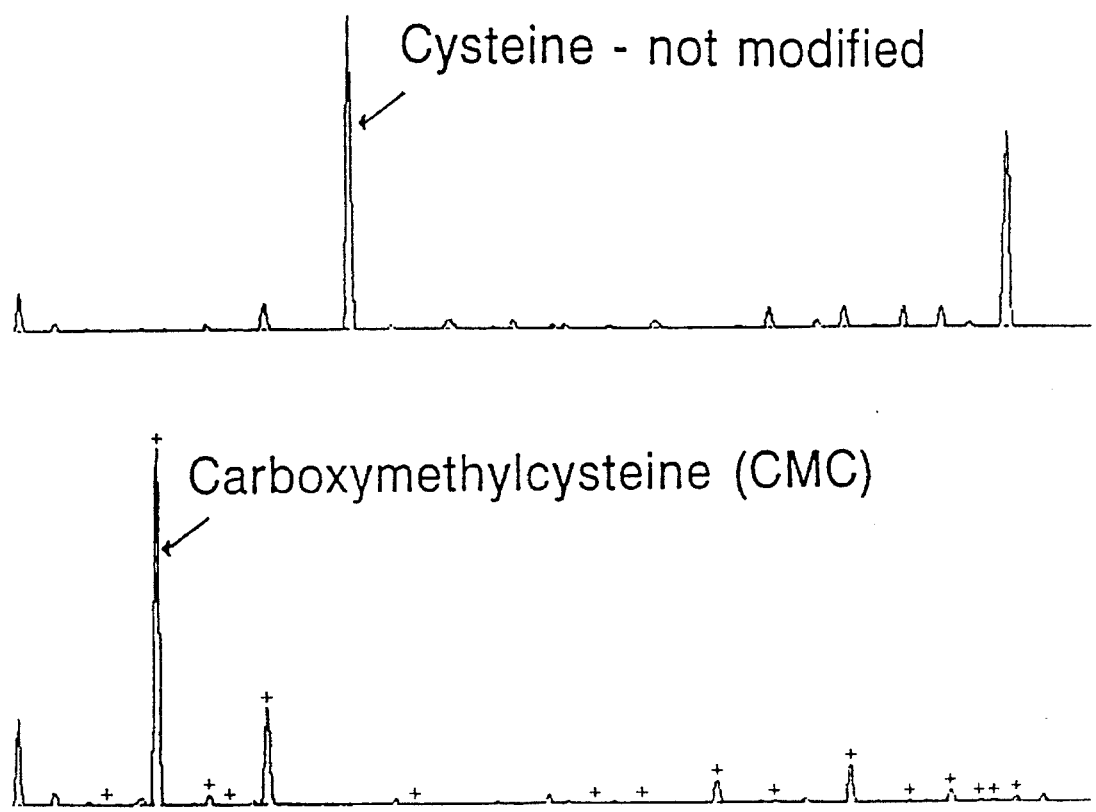
FIG. 11 shows the HPLC results for sequencing cycle 2 of SEQ ID NO:3 following reduction and alkylation of the cysteine residue with iodoacetic acid.

FIGS. 9 and 10 show examples of the theoretical results obtained from the reaction of some commonly employed chemical and enzymatic amino acid cleavage reactants with the control peptides having the sequences shown in SEQ ID NO:3 and SEQ ID NO:4, respectively. FIG. 11 shows the experimental confirmation of the alkylation reaction shown in FIG. 9 for SEQ ID NO:3. (SEQ ID NO:3 was incubated for 2 h at 60° C. in pH 8.6, 0.5M Tris containing 6M guanidine-HCl, 0.3% EDTA, 2% acetonitrile and a 50-fold molar excess of DTT. A 1.2 molar excess of iodoacetic acid was then added and the solution incubated in the dark for 30 min.)

Further confirmation of the utility of the control peptides as controls for chemical and enzymatic amino acid cleavage reactions can be found in the experimental confirmation of the results predicted in FIGS. 9 and 10. For instance, SEQ ID NO:4 is cleaved as predicted when reacted with Endoproteinase Asp-N (SEQ ID NO:4 was incubated at 37° C. for 24 h in ph 8.0, 0.05M sodium phosphate containing 8% acetonitrile and a 1:20 (w/w) ratio of ASp-N to peptide); formic acid (SEQ ID NO:4 was incubated in 75% formic acid for 5 days at 37° C.); and cyanogen bromide (SEQ ID NO:4 was incubated in 70% formic acid containing 3% CNBr in the dark for 15 h).

Although the present process has been described with reference to specific details of certain embodiments thereof, it is not intended that such details should be regarded as limitations upon the scope of the invention except as and to the extent that they are included in the accompanying claims.

What is claimed is:

1. A method for monitoring the performance of an amino acid sequencer during the sequencing of an unknown peptide or protein that is capable of distinguishing between a missed injection sequencer error and an error caused by faulty delivery of chemicals during the sequencer reactions, comprising the steps of:

(1) simultaneously sequencing an internal standard comprising a peptide consisting essentially of unnatural amino acid residues and having an amino acid sequence containing at least two different unnatural amino acid residues, wherein the retention time for each unnatural amino acid residue following derivatization in an amino acid sequencer is distinct from the corresponding retention times for natural amino acid residues, and the unknown peptide or protein in the amino acid sequencer to produce a chromatogram, wherein the retention times corresponding to the unnatural amino acid residues of the internal standard are resolved from the retention times corresponding to natural amino acids; and (2) comparing the retention times corresponding to the residues of the internal standard with predetermined information relating to the internal standard to monitor the performance of the amino acid sequencer.

2. The method of claim 1, wherein two consecutive occurrences of at least one unnatural amino acid residue in the amino acid sequence of the internal standard are separated by at least one differing amino acid residue, further comprising the step of determining the repetitive yield of the two consecutive occurrences to monitor the performance of the amino acid sequencer.

3. The method of claim 1, wherein approximately 70% of the unnatural amino acid residues in the internal standard are positioned in the amino acid sequence so as to be separated by at least one differing amino acid residue, further comprising the step of determining the lag corresponding to each separated unnatural amino acid residue to monitor the performance of the amino acid sequencer.

4. The method of claim 1, wherein the internal standard further comprises a charged substrate or solid support attached at or near the C-terminus of the amino acid sequence, wherein the charged substrate or solid support minimizes wash out of the internal standard from the amino acid sequencer.

5. The method of claim 1, wherein the internal standard comprises a peptide selected from the group consisting of SEQ ID NO:1 and SEQ ID NO:2.

6. The method of claim 1, wherein the peptide consists of at least five unnatural amino acid residues.

7. The method of claim 1, wherein the peptide consists of at least five consecutive unnatural amino acid residues.

8. The method of claim 1, wherein the peptide consists of at least ten unnatural amino acid residues.

9. The method of claim 1, wherein the peptide consists of at least ten consecutive unnatural amino acid residues.

10. The method of claim 1, wherein the peptide consists of between 10 and 40 unnatural amino acid residues.

11. The method of claim 1, wherein the peptide consists of between 10 and 40 consecutive unnatural amino acid residues.

* * * * *